United States Patent
Holtlund et al.

(10) Patent No.: US 9,897,594 B2
(45) Date of Patent: *Feb. 20, 2018

(54) MEMBRANE ASSAY METHOD

(75) Inventors: Jostein Holtlund, Oslo (NO); Andrew Campbell, Oslo (NO); Morten Borch, Oslo (NO)

(73) Assignee: AXIS-SHIELD ASA, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 12/091,254

(22) PCT Filed: Oct. 31, 2006

(86) PCT No.: PCT/GB2006/004058
§ 371 (c)(1),
(2), (4) Date: Nov. 18, 2008

(87) PCT Pub. No.: WO2007/052008
PCT Pub. Date: May 10, 2007

(65) Prior Publication Data
US 2009/0220957 A1 Sep. 3, 2009

(30) Foreign Application Priority Data
Oct. 31, 2005 (GB) .................... 0522193.2

(51) Int. Cl.
C12M 3/00 (2006.01)
G01N 33/50 (2006.01)
C12Q 1/68 (2018.01)

(52) U.S. Cl.
CPC ....... G01N 33/5091 (2013.01); C12Q 1/6806 (2013.01)

(58) Field of Classification Search
USPC .............................. 435/6; 536/23.1
See application file for complete search history.

(56) References Cited

U.S. PATENT DOCUMENTS

| | | | | |
|---|---|---|---|---|
| 4,729,958 A | * | 3/1988 | Drozd et al. | 435/270 |
| 5,128,247 A | * | 7/1992 | Koller | 435/91.53 |
| 5,187,083 A | * | 2/1993 | Mullis | 435/91.1 |
| 5,334,501 A | * | 8/1994 | Adams et al. | 435/6.15 |
| 5,447,864 A | * | 9/1995 | Raybuck et al. | 435/270 |
| 6,465,640 B1 | * | 10/2002 | Hood | 536/25.4 |
| 6,599,713 B1 | * | 7/2003 | Hatanaka | C12Q 1/28 435/28 |
| 8,728,800 B2 | * | 5/2014 | Frantzen | B01L 3/502 435/283.1 |
| 2002/0012982 A1 | * | 1/2002 | Blakesley et al. | 435/183 |
| 2003/0170810 A1 | * | 9/2003 | Vedadi | B01D 15/361 435/69.1 |
| 2004/0241876 A1 | * | 12/2004 | Fannes | 436/514 |

FOREIGN PATENT DOCUMENTS

EP 0588564 A1 3/1994
WO WO 02090995 A2 * 11/2002

OTHER PUBLICATIONS

Urdal, p. et al. Rapid immunometric measurement of C-reactive protein in whole blood. Clin. Chem., vol. 38, No. 4, p. 580-584, 1992.*
Novagen product literature. BugBuster protein extraction reagent, user protocol TB245 Rev. E 0304, p. 1-8, 2004.*
Petter Urdal et al., "Rapid Immunometric Measurement of C-Reactive Protein in Whole Blood," Clinical Chemistry, vol. 38 (4), 1992, pp. 580-584.
Novagen Product Literature, "BugBuster Protein Extraction Reagent," User Protocol TB245 Rev. E 0304 (2004), pp. 1-8.
Nicolaos Christodoulides et al., "Application of Microchip Assay System for the Measurement of C-Reactive Protein in Human Saliva," The Royal Society of Chemistry, vol. 5, 2005, pp. 261-269.
Michele M Doucette et al., "Biochemical and Molecular Action of Nutrients: Palate Receptor Function is Regulated in Response to Different Cellular Growth Rates in Cultured Mammalian Cells," The Journal of Nutrition, Aug. 9, 2001, pp. 2819-2825.

* cited by examiner

*Primary Examiner* — Prabha Chunduru
(74) *Attorney, Agent, or Firm* — Jeffrey N. Townes; LeClairRyan

(57) ABSTRACT

The present invention provides an assay method for a cell-containing body sample, the method comprising treating the sample under conditions whereby to cause cell lysis, preferably by means of a detergent; and subjecting the thus-generated lysed sample to conditions causing the cleavage of nucleic acid molecules. The invention additionally provides the use of nucleic acid cleavage conditions in enhancing a membrane assay, a device for carrying out such an assay, and a kit for use in the assay.

15 Claims, No Drawings

MEMBRANE ASSAY METHOD

The present invention relates to methods for improving the accuracy, reliability and/or speed of assays conducted on body samples. In particular, the present invention relates to high speed assays conducted using membranes or filters of small pore size (e.g. less than 1 μm), especially on samples containing cells or cell debris. most particularly, the present invention relates to methods for improving lysis (e.g. detergent lysis) mediated membrane-concentration assays and corresponding assay kits and devices.

Rapid diagnostic assays are increasingly important for use at the point-of-care (PoC—e.g. at the time of consultation with a medical professional) or in small or rapid-turnaround medical diagnostic laboratories. Such tests, especially for PoC use typically employ at least one "device", such as a disposable tube, stick, cartridge, rotor, etc. which contains volumes for accepting sample(s) plus fluid pathways allowing for specific interactions of the sample with parts of the device, and/or further reagents. Membranes, for instance nitrocellulose, with relatively small pore size, typically 0.2-5 μm, are a commonly used component for rapid diagnostic assays (e.g. immunoassays). Such membranes may be used as the assay's solid phase and are also used for collecting micro particles and precipitated biological materials.

There are two general approaches which can be used for the rapid assay of components in cell-containing samples, such as assay of plasma proteins in blood; one can either separate the cells from the fluid (e.g. plasma) or break down the cells to pass through the membrane. In the separation method, the cells are removed either in a separate process prior to analysis, or by using a filter in the test device itself. In the cell breakdown method, the cell (e.g. blood cell) membranes are fragmented and typically solubilised, for example by using detergents, thus allowing the material to pass through the pores of the membrane.

Rapid tests, particularly for use in point-of-care or streamlined laboratory situations should normally be limited to a small number of (preferably simple) steps and only a few minutes in duration. This renders the use of a separate cell-separation step impractical and means that fluid (e.g. plasma) separation must either take place as an integrated part of the events within the device, or one must make use of lysing agents or conditions, such as detergents, to break up/dissolve cell walls and nuclear membranes to allow the sample to pass through the pores of the filter membrane. Especially with membrane flow-through formats for quantitative assays, the lysis method is beneficial since it is difficult to design efficient blood cell separation with this format.

In assays for use at the point of care, speed, sensitivity and accuracy are all highly desirable factors, but in the context of the assay, it is frequently necessary to make a "trade-off", sacrificing a possible improvement in one factor (such as sensitivity) in order to give acceptable performance in another (such as speed). It would be of great value to provide a method by which these properties could be improved together, such that the balance could be made at a level of overall higher performance.

Membrane flow-through assay formats, also termed immunoconcentration assays, employ small pore size membranes, typically 0.45 μm to which are attached specific binding moieties such as antibodies, receptors, antibody fragments etc. This format demands highly particle-free samples since even small numbers of particles, for instance cell debris, with sizes around or exceeding the pore size of the membrane, efficiently lower the liquid flow through the membrane. In the worst case this can lead to a complete stop of liquid transportation through the membrane, but even minor membrane flow-inhibition can cause flow problems and/or a deterioration in the reliability of the assay. A crucial issue when developing membrane flow-through assays is thus to treat any cell-containing samples in such a way that they pass the membrane without changing the efficient pore size and the flow properties of the membrane during the entire assay.

In addition to the above, haematocrit correction is another problem with quantitative assays based on whole blood which may be addressed by use of lysis (especially detergent lysis) methods. Specifically, by using cell lysis, a simple haemoglobin measurement of the lysate gives the possibility of haematocrit correction.

During (especially detergent-mediated) lysis of whole blood or other cell-containing samples, the main goal is to break down the cell membranes and membranes of the nuclei so as to allow passage through the device, especially through a filter or membrane.

For example, detergents invade the membranes and produces micelles and protein-detergent complexes. The size of the micelles is generally small enough to let them pass through a typical 0.45 um pore size membrane. Similarly, chaotropic lysing agents break up the structure of the proteins supported within the membrane and thus break up its structure.

In spite of the considerable advantages of the (e.g. detergent) lysis method in membrane type assays, very few commercial assays use this method, particularly for automated assay systems. One reason for this may be that membrane blockage and restriction of flow sometimes occurs in circumstances when complete dissolution of the cell membranes into micelles would be expected. Previously, this behaviour has been dismissed as artefactual or has simply not been understood, since the limiting factor for membrane transport in lysis assays has previously been thought of as the break up of the membranes around and within the cells of the sample. In blood samples, for example, inadequate solubilisation of the cell membranes or membranes of the white cell nuclei has previously been thought of as the major cause of membrane blockage.

The present inventors have now, on contrast to the previously understood behaviour of lysed cell samples, unexpectedly established that cellular nucleic acid, especially DNA, even in very small quantities, can cause rate-determining blockage of membranes and high background assay signals.

In a first aspect, the present invention thus provides an assay method for a cell-containing body sample, said method comprising treating said sample under conditions whereby to cause cell lysis; and subjecting the thus-generated lysed sample to conditions causing the cleavage of nucleic acid molecules, especially DNA molecules. Preferably the conditions to cause cell lysis comprise the addition of a cell lysing agent, such as a detergent. Preferably the method is a membrane assay method, more preferably a "membrane capture" assay method, as described below. The method may optionally and preferably comprise (subsequently to passage of the sample through the membrane) assaying the sample (e.g. that part of the sample which passes through the membrane or preferably that part of the sample retained on or by the membrane) for at least one component or potential component in said sample and/or optionally and preferably relating the assayed value to the qualitative, semi-quantitative or quantitative content of the assayed component in the cell-containing body sample, and/or optionally and preferably relating the assayed component to at least one medical or biological condition.

The present inventors' establishment of the cause of membrane blockage in assay devices as being nucleic acids rather than insufficient solubility of the lipid components addresses the need both for improved flow through membranes of small pore size and for decrease in the background signal when such membranes are used for concentrating components in the sample. The improved flow, in turn, allows assays to be conducted more quickly and/or allows a greater volume of sample to be processed in the same period, allowing concentration of analyte from a larger volume and consequent improvement in sensitivity and accuracy.

In a further aspect, the present invention thus provides the use of nucleic acid cleavage conditions in an assay method comprising the flow of lysed cell-containing body sample through a membrane of pore size no greater than 10 μm. This use is in improving the performance of the assay and may take one or more forms, or may be an improvement in the overall balance of properties. Preferably the use is in enhancing fluid flow through the membrane and/or in reducing the background signal on the membrane and/or increasing the speed of the assay, in a membrane concentration assay.

In a still further aspect, the present invention also provides an assay device incorporating a chamber for accepting a cell-containing body fluid and at least one membrane of pore size no greater than 10 μm, wherein said device in use provides nucleic acid cleavage conditions. Preferably, the device contains at least one chemical and/or biological means for nucleic acid cleavage, such as those described herein infra. Conditions for nucleic acid cleavage will then be provided by use of the device.

In a yet still further aspect, the present invention provides a kit for assay of a cell-containing biological fluid, said kit comprising; a device comprising a membrane of pore size less than around 10 μm; and at least one chemical and/or biological means for nucleic acid cleavage. Optionally and preferably, the kit will contain at least one means for cell lysis, such as a detergent and/or at least one reagent for assay of a component or potential component of said sample. Further optionally and preferably, the kit will contain instructions for use in a method comprising lysis (e.g. detergent mediated lysis) of said cells, followed by cleavage of the thus-released nucleic acid molecules, followed by passage of at least part of the resulting sample through the membrane. Most preferably this method is a method of the invention as described herein.

The conditions for causing cleavage of nucleic acid chains as referred to herein may be physical conditions (such as shaking, mixing, vortexing etc.), radiative conditions (such as treatment with electromagnetic radiation, such as UV, x-ray or γ-ray radiation), chemical conditions (such as control of the pH and/or red-ox conditions) and/or biological conditions (such as treatment with enzymes and/or activation of endogenous enzymes having nucleic acid lysis properties, such as nucleases). Preferred conditions for causing nucleic acid cleavage are radiative, chemical and biological conditions, especially treatment with at least one added and/or endogenous enzyme.

The present inventors have extensively examined the causes of membrane blockage in assays comprising the flow of detergent lysed cell-containing samples (especially blood) through small pore membranes. As with others of skill in the relevant art, they began with the assumption that membrane flow was controlled by the transformation of membranes into micelles, typically mediated by detergent. It came as a remarkable surprise to the inventors that the very small relative mass of DNA in a sample, especially a blood sample, could have any noticeable physical effect, especially in blocking membranes.

Normal human blood contains about one leucocyte for every 1000 red blood cells. Red cells do not contain a nucleus or DNA while white cells are nucleate and contain DNA. A typical mammalian cell contains 70% water, 3% phospholipids, 1.1% RNA and 0.25% DNA among other constituents. A typical mammalian cell membrane contains about 50% phospholipids and 50% membrane bound proteins. This means that cell membranes constitute approximately 20% of the dry weight of a mammalian cell compared to 0.8% DNA. Looking at the white blood cells only, the mass ratio membranes:DNA is about 25:1. Taking into consideration the erythrocytes with a membrane but no DNA, the mass ratio membranes:DNA for all blood cells taken together is probably about 1000:1.

Initially, an assay was conducted manually in which high shear forces were employed. This assay showed no problems with membrane blockage or high background signals. In the manual assay, whole blood was taken from a finger stick and subsequently lysed by dilution in a liquid containing the detergent deoxycholate by vigorous shaking for some seconds. The lysed blood was in the next step filtered through the membrane coated with antibodies, thus capturing the analyte. Upon addition of gold-conjugated antibodies followed by a washing solution, a red signal developed from the gold particles was measured.

Subsequently, the inventors developed an automated version of the manually operated assay briefly described above. In this instrumented assay the blood is gently mixed with the dilution liquid by pumps contained in the instrument. When analysing blood samples with this instrument, some samples showed unusual flow properties through the nitrocellulose membrane. In some cases the flow was slow and in a few cases the liquid flow through the membrane came to a full stop. It was noted that the dilution liquid contained more detergent than needed for complete lysis of blood samples containing very high number of red blood cells (hematocrit 80%). The blood samples with reduced flow rate consistently gave severe overestimation of the analyte concentration using the plasma results from the same samples as reference.

DNA from the human genome is very long, up to 5 cm, and these strands are very vulnerable to shear forces. In the hand-prepared sample, the shaking was hypothesized to break up the DNA, whilst in the instrument the blood sample was mixed with the dilution liquid in a very gentle way and the DNA structure preserved, allowing the DNA to block the membrane. The inventors prepared hand-prepared samples mixed only gently and found that membrane blockage also occurs. Similarly, shaking the sample vigorously before processing in the instrument resulted in the flow rate being normalized with no membrane blockage, and correct determination of plasma analyte concentrations. Samples with a high proportion of white blood cells (which contain DNA), were found to be more likely to result in membrane blockage, than normal samples or samples with a high proportion of red blood cells (which do not contain DNA).

These observations together supported the inventors' hypothesis that DNA contained in the nuclei of white cells was the source of the flow problems. This was then further verified by experiments with chemical and particularly biological methods of nucleic acid digestion. These experiments also indicated that in addition to causing membrane blockage, long chains of nucleic acid could also provide a very high background signal in membrane flow through assays, thereby causing false positive or simply inaccurate results.

In the assay method of the present invention, a cell-containing sample is lysed by treatment under appropriate conditions so as to break up cellular and nuclear membranes. In a preferred embodiment, the sample is treated with at least one detergent to provide cell and membrane lysis, followed by breaking up of nucleic acid molecules.

The "detergent" as indicated herein may be any amphiphilic molecule capable of facilitating the conversion of phospholipid membranes into small structures such as micelles and/or vesicles capable of passing through a small pore membrane (as describe herein). Suitable detergents include cationic, anionic, zwitterionic and non-ionic surfactants, but particularly anionic surfactants. Particular examples include; cholate detergents including sodium cholate, sodium deoxycholate (DOC); Polyoxyethylene the series of detergents, such as Triton, Tween, Genapol, Lubrol, Thesit, Brij and Lubrol; and other detergents including sodium dodecylsulfate (SDS), dodecyl-beta-D-maltoside and octyl-beta-D-glucoside, N-lauroylsarcosine sodium salt, lauryldimethylamine-oxide (LDAO), cetyltrimethylammoniumbromide (CTAB) and bis(2-ethylhexyl)sulfosuccinate sodium salt. Although sodium salts are mentioned, evidently salts with other metals such as potassium, magnesium etc would be equally effective. A most preferable detergent is sodium deoxycholate.

Although the use of detergents is a preferred method of cell lysis for use in the present invention, the invention is equally suited for use with many other methods of cell lysis including hypo or hypertonic lysis, chaotropic lysis etc. Suitable reagents for use in such methods will be known to one of skill in the art and include: deionised water (for hypotonic lysis); tonicity adjusters, such as salts including sodium, magnesium and potassium salts (e.g. NaCl, KCl), for hypertonic lysis; and chaotropic agents, such as chloroform, phenol or chaotropic salts including guanidinium isothiocyanate (GuSCN) or urea.

As used herein, the term "nucleic acid" is intended to indicate macromolecular chains of ribonucleic acid (RNA) and/or deoxyribonucleic acid (DNA), both in pure form and, more commonly in their natural form in complex with other molecules including macromolecules such as polypeptides/proteins. In particular, genomic DNA from a mammalian sample will generally exist as a complex of nucleosomes and linker regions, in combination with other factors such as chromatin or associated proteins. Preferably, the nucleic acid referred to herein is DNA and in particular genomic DNA.

In all aspects of the present invention, conditions suitable for causing cleavage of nucleic acids are, as indicted herein supra, typically physical, radiative, chemical and/or biological conditions. Preferable conditions are chemical and/or biological conditions for causing nucleic acid chain cleavage. Chemical cleavage of DNA can be caused by any suitable reagent including a variety of well known DNA damaging agents such as epoxides, imines, activated cyclopropanes, hetrocyclic N-oxides, quinines etc. Preferably, these "chemical nucleases" will be redoxactive coordination complexes that cleave DNA by an oxidative pathway. Preferred examples include copper phenanthroline followed by an oxidising agent, diazonium salts, photocleavage using metal complexes and ferrous/EDTA systems.

"Biological" methods of nucleic acid cleavage may be conducted with any suitable nuclease, generally under mild conditions. A nuclease suitable for use in the present invention is an enzyme capable of cleaving the phosphodiester bonds between the nucleotide subunits of nucleic acids. Many types of nuclease of varying activity, metal dependence and specificity are known including the "restriction enzymes" commonly used for generating DNA fragments in genetic manipulation experiments. These include nucleases dependent upon ions such as magnesium and calcium. Calcium dependent nucleases are one preferred group for use in the present invention, as are magnesium dependent nucleases. Any of these nucleases are suitable since cleavage of the nucleic acid chain into even moderate length fragments will generally be sufficient to allow unrestricted passage of the sample through the membrane.

Common examples of nucleases include micrococcal nuclease (S7 Nuclease), S1 Nuclease, Mung Bean Nuclease, DNase I, Nuclease BAL 31 Benzonase™. One particularly suitable nuclease is Micrococcal nuclease (also called *Micrococcus* nuclease since it derives from *Micrococcus pyrogenes*), a $Ca^{2+}$ dependent endonuclease which preferentially cleaves DNA within the linker region between the 11 nm diameter nucleosomes. The degradation of DNA can be followed by the reduction of viscosity of the very viscous solution of uncleaved DNA.

In the Examples below, 0.1-0.5 U/ml *Micrococcus* nuclease was added to blood samples lysed with detergent, together with 1 mM $CaCl_2$ and incubated for 30 sec prior to membrane flow-through analysis. The liquid flow rates and assay results were normalized even for blood samples with high ($35 \times 10^9$/L) white cell counts. Omission of $Ca^{2+}$ gave the same slow flow and false high assay determinations as the control with no nuclease added.

Most biological material, such as nucleases are inherently unstable in aqueous solutions. It is therefore an advantage if the nucleases can be stabilised such that they may be stored for long periods as part of the devices and/or kits of the present invention. In one embodiment of the invention, nucleases are thus provided in dried form, and the enzymes are thus dried before incorporation into a diagnostic assay device or kit A preferred method of drying nucleases is using standard freeze-drying methods, however other methods for drying reagents could readily be employed by those skilled in the art, for example spray-drying or vacuum-drying.

In one embodiment, the nuclease is dried as single assay units, for example dried on a reaction well, such as onto at least a part of the inside surface of a chamber or container. In a preferred embodiment the nuclease reagent is provided as at least one dried (e.g. freeze-dried) reagent particle (e.g. bead or sphere). Spherical freeze-dried particles are known from Price et al. (U.S. Pat. No. 3,655,838). The disclosed spherical beads contain material for immunological reactions and are commonly referred to as lyospheres. Lyospheres of certain materials are known for instance from U.S. Pat. No. 3,932,943, and these known methods may readily be applied by one of skill in the art to the nucleases for use in the present invention. For the production of lyospheres, see for example Wiseman, William Howard, January 1958 Thesis (Ph. D)—Institute of Paper Chemistry, 1958. and U.S. Pat. No. 3,655,838). These and all reference cited herein are hereby incorporated herein, in their entirety, by reference.

Where drying methods, such as freeze-drying are used, standard croyprotective, lyoprotective and/or rehydration enhancing agents may be used to enhance the properties of the dried reagent. Typical agents include salts and sugars, particularly trehalose, lactose, sucrose, proline, mannitol, raffinose, and sodium lactate. Trehalose is particularly effective.

The method of the present invention may additionally comprise assaying the lysed and treated (to break nucleic acid chains) sample for at least one component or potential component of the sample. Suitable components for assay include any of a wide variety of biological markers including small molecules (such as amino acids), vitamins, oligo- and poly-peptides (including antibodies, proteins and protein complexes), peptide and non-peptide hormones and many others. Since the assay is generally a detergent mediated cell lysis assay, membrane-bound components such as receptors may also be assayed. Assays for proteins, vitamins, amino acids and/or cofactors in plasma are particularly enhanced by the present method. Specific examples include C-reactive protein (CRP), cobalamin, transcobalamin (especially holo transcobalamin), homocysteine, folate, folate receptors and combinations thereof. Accute phase markers such as CRP are particularly suitable.

The optional but preferable step of assaying for a sample component may be carried out in any of the many formats which are well known in the art. Of particular benefit in the present invention, however, is assay for a sample component by a membrane assay, especially a membrane concentration assay. In an assay of this type, a specific binding ligand, such as an antibody, receptor, or antibody fragment, complex or derivative (e.g. single chain antibody) is immobilised on the membrane and serves to capture and concentrate the analyte of interest. This captured analyte may then be detected directly, or more commonly will be bound by a further (specific or non-specific) binder (such as an antibody) which in turn will be bound or conjugated to a signal forming moiety. Such signal forming moieties my be radioactive, coloured, fluorescent, chemi- or bio-luminescent or capable of reacting or processing a substrate to generate any detectable signal. The assay then typically involves detecting the detectable signal and optionally comparing this to predetermined values or standards to determine (in a qualitative, semi-quantitative or quantitative way) the concentration of the component of interest in the original sample.

A particularly preferred format of the present invention comprises contacting a cell-containing body sample (preferably a whole blood sample) with lysis conditions such as a detergent (e.g. DOC) and a biological or chemical "nuclease" (such as Micrococcal nuclease) in the presence of any necessary metals or cofactors (such as $Mg^{2+}$ or $Ca^{2+}$). The resulting sample is then contacted with a membrane having pores no greater than 10 µm, preferably no larger than 2 µm (e.g. around 0.45 µm) having immobilised thereon a specific binding ligand (such as an antibody) for a component of the sample (such as CRP). Once the sample has flowed through the membrane, the membrane or support is then treated with a further binder (such as a further antibody) for the sample component bound to a signal-generating moiety (such as a gold complex). The signal-generating moiety is then detected (e.g. colourimetrically) to give a value or indication (e.g. any combination of low, normal, slightly elevated or highly elevated) of the component concentration in the cell containing sample. Such an assay may optionally include an additional step of assessing the total cell count or cell count of a specific cell type and optionally correcting or relating the measured value by or to this cell count. For example, a red cell count (Haematocrit) value and if desired, correction, may be applied for a blood sample by colourimetric measurement of haemoglobin using standard methods.

In any of the methods of the present invention, the nucleic acid cleavage will preferably be conducted prior to contact of the sample with a separation membrane, but may alternatively occur after the sample has been applied to such a membrane.

In this latter case, the nucleic acid is cleaved on the membrane, typically by addition of suitable chemical or biological agents (as discussed herein) after application of the sample to the membrane. Alternatively, the cleavage reagent may be placed on, in, around and/or near to the membrane. This might be in the form of a dried coating or particle.

Evidently, more than one component in the sample may be assayed for by provision of more than one membrane and/or more than one immobilised specific binder, providing that the signals from the different components may be identified e.g. by spatial separation (presence on different membranes or membrane regions) or by use of differing and separable signals (e.g. two fluorophores with differing excitation and/or emission wavelengths).

Having assayed for at least one component of a sample, the generated qualitative or (semi-)quantitative value may then optionally be related to a specific biological condition or disease, or used as a weighting or contributory factor in the diagnosis of a disease or biological condition. High CRP, for example may be related to acute inflammation, inflammatory rheumatic diseases, and/or to the need for, or effectiveness of, treatments for such conditions.

The present invention provides for the use of nucleic acid cleavage conditions to reduce membrane blockage in an assay method comprising the flow of a detergent lysed cell-containing sample through a membrane of pore size 10 µm or less (preferably 2 µm or less). Generally, two interrelated improvements are facilitated and either or both may be important in any particular assay. Essentially, the nucleic acid cleavage reduces membrane blockage and this improvement has two primary results; the flow of fluid through the membrane is enhanced, and/or the non-specific entrapment of components from the sample is reduced. Each of these then has additional advantages in that better flow provides for faster and/or more reliable assays and reduced non-specific binding allows for lower background signals, higher sensitivity and greater discrimination in the assay. Evidently, the "use" provided by the present invention may be use in any of the methods described herein may employ any of the chemical or biological reagents or other techniques described herein and elsewhere to generate nucleic acid cleavage conditions. Nuclease mediated cleavage is particularly favoured.

As referred to herein, "membranes", where context permits, are porous membranes having a pore size no greater than 10 µm, preferably no more than 5 µm (e.g. 1 µm or less) and more preferably 0.5 µm or smaller. Membranes of around 0.45 µm pore size are particularly suitable. Although the minimum pore size of the membrane is limited only by the requirements of sufficient flow and the need for appropriate components to pass through the membrane, typical minimum pore sizes will be at least 50 nm, preferably at least 100 nm, more preferably at least 200 nm. The membrane material may be any material which is stable to the passage of a suitable sample, which will generally be aqueous based but may contain added solvents as appropriate. Nitrocellulose membranes are particularly suitable, as are those of glass, polyethylenes, polypropylenes, fluoropolymer (e.g. PTFE or PTFE blends or copolymers), polyamide and blends and copolymers thereof. Nitrocellulose is most preferred.

The samples referred to herein in all aspects of the invention are, where context allows, cell-containing samples or samples derived therefrom. A cell-containing sample may be of any type of tissue and may comprise cells of any type. Most typically these will, however, be fluid samples, of which blood and seminal fluid are preferred cell-containing samples. Whole blood, with or without additives to improve storage properties and/or reduce coagulation is the preferred cell-containing sample and is used as illustrative herein. Evidently, such blood samples may be treated as necessary for performance of the assay (e.g. to free bound components for assay or extract competing analytes), but where possible, the maximum number of steps should be carried out within the device, to minimise the time and handling required.

The device of the present invention comprises a chamber for accepting at least one cell-containing body sample (or optionally but less preferably a detergent lysed cell-containing sample) and contains at least one membrane as described herein. The device may optionally be pre-loaded with at least one lysing agent, such as a detergent, to provide cell lysis or may comprise a chamber into which such an agent may be added. Cell lysis will be carried out before passage through the membrane and the device provides conditions for nucleic acid cleavage which optionally and preferably will occur during or immediately subsequent to cell lysis.

The device will preferably comprise at least one biological and/or chemical reagent for causing nucleic acid cleavage, as described herein, or will comprise a chamber for accepting the addition of such a reagent. The device will also preferably contain or accept a specific binder for concentrating at least one component of the sample, a second (specific or non-specific) binder for attaching to the concentrated component and at least one signal generating moiety where by to generate a signal corresponding to the presence, absence or concentration of the component of interest. All of these entities are described herein and will be well known to those of skill in biological assays. The membrane comprised in the device of the invention may preferably serve to immobilise at least one specific binding ligand for at least one component or possible component of the prospective sample. Suitable binders are described herein. Alternatively, the specific binding ligand may be immobilised on a support, such as a bead or insoluble particle, which is then retained by the action of the membrane.

One preferred device comprises a chamber for accepting a blood sample; a chamber for accepting a diluent comprising a detergent (such as DOC), a nuclease (such as Micrococcal nuclease) and any metal or cofactor (such as $Ca^{2+}$); a membrane having pores no larger than 10 μm, preferably 2 μm (e.g. around 0.45 μm) and having immobilised thereon a specific binding ligand (e.g. and antibody or a fragment, construct or derivative thereof) for at least one analyte (e.g. CRP, holoTC, SAH); and a chamber for accepting a solution comprising at least one additional binder and optionally a signal generating moiety. The device may additionally comprise a region, cuvette or window for assessing a signal generated from the signal generating moiety and corresponding (directly or indirectly) to the presence, absence or concentration of the component of interest.

In a related and sill more preferable device, the device comprises a chamber for accepting a blood sample, a chamber either containing or suitable for accepting a detergent and a chamber containing a nuclease, dried in accordance with known methods and/or those methods described herein. These may be three separate chambers, or preferably will be one or two chambers, for example, one containing the detergent and a second containing the dried nuclease. The device will and may contain other features as described above.

A number of formats are suitable for the device of the present invention including tubes, rotors, cartridges, vials, slides, sticks etc. Many such formats are well known but the nature of the format is not critical providing that the essential features of the device can be provided. Rotor and cartridge formats are highly suitable because pressures for enhancing the passage of fluid through the device may easily be provided. Any of the devices of the invention may comprise a region, cuvette or window for assessing a signal generated in operation of the device.

The kits of the present invention will frequently comprise at least one device of the invention and, at least, the kits will comprise a membrane, and a means for nucleic acid cleavage (such as a chemical or biological reagent including those described herein). Typically, a detergent for cell lysis and conversion of membrane lipids into small micelles/vesicles will be provided, as may reagents and/or instructions for use of the kit in any of the methods described herein.

The kits and devices of the present invention will most preferably be suitable for use in or with automated analysis equipment. Most suitably, this will be "point-of-care" automated analysis equipment.

One preferred kit comprises an optional means for obtaining a blood sample; a vessel for accepting said blood sample and a diluent comprising a detergent (such as DOC), a nuclease (such as Micrococcal nuclease), any metal or cofactor (such as $Ca^{2+}$) and optionally a buffer; a membrane having pores no larger than 2 μm (e.g. around 0.45 μm) and having immobilised thereon a specific binding ligand (e.g. and antibody or a fragment, construct or derivative thereof) for at least one analyte (e.g. CRP, holoTC, SAH); and a vessel or chamber for accepting a solution comprising at least one additional binder and optionally a signal generating moiety. The kit may optionally and additionally comprise instructions for use, assessment of the result of the assay and/or correlation of the result to biological conditions.

A particularly preferred kit comprises an optional means for obtaining a blood sample; a vessel for accepting said blood sample and a diluent comprising a detergent (such as DOC). The vessel, or a second vessel in the kit will also contain a nuclease in dried form (such as Micrococcal nuclease), and any metal or cofactor (such as $Ca^{2+}$) necessary. The kit will also contain; a membrane having pores no larger than 2 μm (e.g. around 0.45 μm) and having immobilised thereon a specific binding ligand (e.g. and antibody or a fragment, construct or derivative thereof) for at least one analyte (e.g. CRP, holoTC, SAH); and a vessel or chamber for accepting a solution comprising at least one additional binder and optionally a signal generating moiety. The kit may optionally and additionally comprise instructions for use, assessment of the result of the assay and/or correlation of the result to biological conditions and may optionally also contain a buffer in dried or solution form.

The invention will be illustrated below by reference to the following non-limiting examples.

EXAMPLES

Example 1

Whole blood from a healthy donor was centrifuged on the density gradient medium Polymorphprep™ (Axis-Shield PoC AS, Oslo, Norway) as described by the producer. Total white blood cells and red cells were collected in two separate fractions. White cells were counted. White cells were added to whole blood to increase the number of white cells from $7 \times 10^9$/L to $30 \times 10^9$/L. 12.5 μl of the enriched blood was added to 1 ml of dilution liquid (buffered Na-deoxycholate) containing 1 mM $CaCl_2$. This solution was divided in two aliquots of 500 µl, one of them were subsequently added 2.5 µl (0.25 U) Micrococcal nuclease. Aliquots of 50 µl of the control solution and the nuclease containing solution were applied to a membrane flow through device (NycoCard Test Device) containing a 0.45 µm pore size nitrocellulose membrane. Aliquots were applied 0 sec, 60 sec and 120 sec after addition of the nuclease. When the blood cell lysate had soaked through the membrane in a flow through manner, 50 µl of a gold conjugated antibody was added followed by 50 µl of washing solution. It should be noted that the membrane bound antibody and the conjugated antibody were directed against different proteins meaning that no sandwich could be formed and that the experiment just shows non specific binding of gold conjugated antibody to the membrane. The red colour of the retained antibody on the membrane was measured using a reflectometer (NycoCard Reader). This instrument expresses the density of the colour as K/S which is proportional to the amount of gold labelled antibody trapped onto the membrane. A white membrane will give a K/S of approximately 0.05 while a very dense, deep red colour will give a K/S of about 5.

| | K/S after x seconds | | |
|---|---|---|---|
| Seconds | 0 | 60 | 120 |
| Control | 0.71 | 0.89 | 1.24 |
| Nuclease | 0.154 | 0.123 | 0.136 |

The table shows for the control a high non-specific background increasing over the incubation period while the background is down to a normal low level (as low as for a plasma-based analysis) even with the first aliquot with less than 30 seconds incubation.

Example 2

In this experiment whole blood was enriched in white cells without the use of density gradient medium centrifugation as was done in example 1. Whole blood from a healthy donor was centrifuged at 2500×g for 15 minutes. The plasma was pipetted off and subsequently the buffycoat and part of the red cell fraction was pipetted off. The buffycoat fraction contained red cells enriched in white cells. Finally pure red cells were taken from the bottom of the tube. The fraction enriched in white cells and the red cell fraction were added to plasma to give the same haematocrit as whole blood and white cells were counted in all three fractions. Haemoglobin was measured spectrophotometrically at 200 times dilution in distilled water at 575 nm using a Shimadzu spectrophotometer.

| | $O.D._{575\,nm}$ | white cells/L |
|---|---|---|
| Whole blood | 0.672 | $7.5 \times 10^9$ |
| Enriched in w.c. | 0.657 | $34 \times 10^9$ |
| Red cells | 0.690 | 0 |

These three fractions will hereafter be termed C (whole blood), W (blood enriched in white cells) and R (red cell fraction).

5 µl of C, W and R respectively were gently mixed with 400 µl dilution liquid and 50 µl of each solution applied to a NycoCard test device followed by 50 µl gold conjugated antibody and 50 µl washing solution. As described in example 1, the conjugate antibody and the membrane bound antibody were directed to different proteins. In other words this experiment shows non-specific background only. The lysed dilutions of C, W and R were then shaken vigorously for 10 seconds and 50 µl of each processed in the membrane test device as described above. The conjugate background was measured for both series using the NycoCard Reader.

| | K/S | K/S shaken sample |
|---|---|---|
| C | 0.136 | 0.097 |
| W | 0.422 | 0.112 |
| R | 0.088 | 0.094 |

The table shows that the non-specific background was highly elevated in the case of W and slightly elevated with C compared to the background obtained with a pure red cell fraction (R). Shaking reduced the background of C and W to the same level as for R.

5 µl of C, W and R were in the next experiment gently mixed with 400 µl of dilution liquid containing 1 mM $CaCl_2$ and 0.4 U Micrococcus nuclease and processed in the test devices as described above.

| | K/S |
|---|---|
| C | 0.12 |
| W | 0.108 |
| R | 0.094 |

It appears from the table that nuclease digestion of the samples reduced the backgrounds down to "shaking level". The same advantageous low background was obtained with breaking down DNA either with shearing forces or with enzymatic digestion of DNA. Shaking of the nuclease digested samples did not lower the background further (not shown).

Examples 1 and 2 demonstrated how nuclease digestion of detergent solubilized whole blood reduced the non-specific background in the membrane flow-through test device down to a low level which is the same as the background we obtain with plasma based analysis. The next two examples shows the effect of nuclease treatment when diluted and lysed blood samples were analysed for CRP (C reactive protein) in our automated analyser which is based on the same membrane flow-through system as the manually operated test devices described in examples 1 and 2.

It should be kept in mind that this analyser mixes the small volume of whole blood (1.5 µl) taken from a finger stick with the dilution liquid (200 µl) in a very gentle way. In other words, shearing forces to degrade the DNA released from the lysed white cell nuclei are absent or too small to work efficiently.

Example 3

The blood samples C, W and R described in example 2 were analysed using the automated analyser. The blood was either lysed in the normal dilution liquid or in dilution liquid containing 5 mM $CaCl_2$ and 0.2 U Micrococcal nuclease.

|  | Control dilution liquid | | Dilution liquid + nuclease | |
|---|---|---|---|---|
|  | CRP, mg/L | HCT, % | CRP, mg/L | HCT, % |
| Plasma | 0.93 |  | 1.37 |  |
| C | 2.49 | 42.7 | 1.59 | 43.6 |
| W | 8.8 | 45.0 | 2.70 | 45.0 |
| R | 1.72 | 43.6 | 1.93 | 46.4 |

It appears from the table that the CRP-concentration in the blood sample is about 1 mg/L (plasma based determinations). This is a typical value for a healthy person. Using blood, one must expect a slight elevation of the background due to the red colour of the haemoglobin. This means that the CRP-values for sample R (red cells and no white cells) are the base line or the target value for CRP. Looking at the results obtained with the control dilution liquid, it appears that the CRP result was increased by 45% for the normal whole blood and 512% for the preparation enriched with white cells. Using dilution liquid with nuclease, no CRP increase was observed with whole blood and an increase of 40% was found with the white cell enriched preparation. The conclusion is that CRP was significantly over-estimated when normal dilution liquid was used for dilution of sample W (high white cell counts). It seems that that this sample was slightly over-estimated also when using nuclease. This indicates that higher concentration of nuclease should have been used in this experiment. HCT (haematocrit) determinations show that these were similar for all 3 samples.

Example 4

Three blood samples with low, medium and high plasma concentration of CRP were analysed on the instrument. All three samples had high white cell counts. A normal cell count is about $7\times10^9$

| Sample | CRP, mg/L | white cell count |
|---|---|---|
| 1 | 1.3 | $29.6 \times 10^9$ |
| 2 | 17.2 | $23.5 \times 10^9$ |
| 3 | 136.8 | $26.6 \times 10^9$ |

The samples were analysed using normal dilution liquid or dilution liquid containing 5 mM $CaCl_2$ and 0.5 U Micrococcal nuclease. Based on the conclusions in example 3 the concentration of nuclease was raised from 0.2 (example 3) to 0.5 U in this experiment. The coefficient of variation (CV) was also determined based on 4-6 parallels. CV was not calculated for sample 1 due to the very low value of CRP.

|  |  | Control dil. liquid | | Dilution liq. + nuclease | |
|---|---|---|---|---|---|
| sample |  | CRP | CV | CRP | CV |
| 1 | Plasma | 1.3 |  | 1.5 |  |
|  | Blood | 23.7 |  | 2.6 |  |
| 2 | Plasma | 17.2 |  | 19.5 |  |
|  | Blood | 31.8 | 10.2 | 16.3 | 1.7 |
| 3 | Plasma | 136.8 |  | 137.3 |  |
|  | Blood | 160 | 10.1 | 123.7 | 3.0 |

The table shows that the CRP-concentration for all 3 blood samples is over-estimated when the normal dilution liquid was used. The lower the CRP-concentration, the worse was the discrepancy between the determination using blood vs plasma. The determinations using plasma is regarded as the correct value. Especially severe is the discrepancy with samples containing low CRP-concentrations. Sample 1 was over-estimated 1800%, sample 2 185% and sample 3 117%. This was to be expected if we assume the same fixed non-specific background contribution with all 3 samples.

Using dilution liquid containing nuclease, the situation was quite different. Whole blood determinations were for all 3 samples similar to the plasma values.

Furthermore, the CV of the determinations was significantly lower when nuclease was included in the dilution liquid.

The conclusion was that nuclease mediated DNA-degradation of the lysed blood samples gave a remarkable quality improvement of the automated CRP-assay.

Example 5

Whole blood from a healthy donor was processed as described in Example 2. Whole blood (C), blood enriched in white cells (W) and red cells (R) showed the same haematocrit. White cell counts were $5.9\times10^9$, $16.9\times10^9$ and $0\times10^9$/L, respectively. 25 µl "blood" sample was added to 400 µl buffered detergent containing 2 mM $MgCl_2$ with or without 1 U nuclease. The blood was mixed very gently with the lysis solution in order to reduce shearing forces to a minimum. 50 µl of this solution was added to a membrane flow-through device (membrane area 9.4 $mm^2$) and flow time taken. The membrane was coated with anti-CRP antibodies. Subsequently 50 µl gold-conjugated anti-CRP antibody was added followed by 50 µl washing solution. The membrane colour was finally measured using a reflectometer (NycoCard Reader). In this example the red colour on the membrane will represent a true CRP-signal plus a greater or lesser amount of non-specific background signal.

| Sample | Flow time (sec) | Colour (K/S) |
|---|---|---|
| C | 38 | 0.81 |
| C + nuclease | 22 | 0.313 |
| W | 188 | Nd ** |
| W + nuclease | 23 | 0.310 |
| R | 25 | 0.27 |
| R + nuclease | 23 | 0.306 |
| Plasma * | 24 | 0.322 |

* 15 ul plasma was used to give the same plasma load as with the blood samples.
** The conjugate did not pass the membrane due to clogging. The colour was dark red.

The table shows that whole blood (C) gave a significant increase in flow time compared to the nuclease treated sample. With sample W the flow time increased dramatically (8 times) and the liquid flow came to a full stop during the application of the gold conjugate. All samples showed the same good flow of about 23 sec when nuclease was added. This was the same flow time as with plasma and with the red cell fraction without nuclease. With respect to signal, whole blood without nuclease would have resulted in a very significant over-estimation of CRP, With W, the flow came to a full stop due to DNA mediated membrane clogging.

Upon nuclease treatment all three samples gave very similar CRP-signals of about 0.31, close to the signal obtained with plasma (0.322) which should be regarded as the target value. This low signal was well above the colour obtained with a membrane coated with an irrelevant antibody (0.093), which represents the background value that would have been obtained with a sample containing zero CRP. This is therefore a low but significant signal of 0.31, and is consistent with the low CRP level of a healthy blood donor.

Example 6

When analysing low concentration blood analytes it is advantageous to process as much blood as possible in order to partly compensate for the low concentration and obtain a readable signal. This experiment was designed to determine the highest possible amount of blood that could be processed through a 0.45 µm nitrocellulose membrane (flow area 9.4 mm$^2$) upon detergent mediated blood lysis.

Due to the large amount of blood used in parts of this experiment, a high concentration of detergent had to be used to ensure that deficiency of detergent would not be the reason for poor flow.

Blood from a healthy donor (white cell count 6.5×10$^9$/L) was diluted with the buffered detergent with or without 1 U of nuclease and incubated at room temperature for 30 sec (incubation volume 200 µl). 100 µl of this solution containing from 1.5-25 µl whole blood was added to the flow-through device followed by 50 µl gold conjugated anti-CRP antibody and 50 µl washing solution. Total assay time (start of sample application to end of washing solution) was measured.

| Volume blood processed (µl) | Total assay time (sec) |
|---|---|
| 25 | Nd* |
| 25 + nuclease | 189 |
| 12.5 | 672 |
| 12.5 + nuclease | 142 |
| 6.25 | 291 |
| 6.25 + nuclease | 128 |
| 3.1 | 264 |
| 3.1 + nuclease | 128 |
| 1.5 | 150 |
| 1.5 + nuclease | 120 |

*membrane blockage during sample application

The table shows that nuclease digestion of DNA resulted in improved flow at all levels of blood load. Looking at assay time, it appears that 12.5 µl blood with nuclease digestion gave about the same assay time as 1.5 µl blood without nuclease, a factor of about 8. Looking at the results from another angle, if we demand a total assay time for a rapid test to be below 4 minutes, this system tolerates 1.5 µl blood without nuclease and 25 µl with nuclease digestion, a factor of 16.7. Broadly speaking, nuclease mediated digestion of DNA allows at least 10 times more blood to be processed in this immune-concentration test device.

Example 7—Nuclease Freeze-Drying Procedure

Benzonase™ was prepared at a concentration of 40 U/ml in a buffer containing 12% Trehalose, 0.1% BSA, 1 mM MgC$_{12}$, 25 mM Tris pH 7.4. Aliquots of this Benzonaze™ solution was frozen then freeze-dried at −30 degree C. in a manner known per se.

Example 8—Use of a Freeze-Dried Nuclease

Frozen and freeze-dried Benzonase™ beads (as prepared in example 7) were placed into an Afinion™ Analyser CRP cartridge and a blood sample containing elevated white blood cells was processed using the Afinion™ Analyzer. The relative activity of the Benzonase™ was calculated by using the normalized CRP values and expressed as a percentage Relative Nuclease Activity in an Afinion™ CRP Assay:

A.—Benzonase™ was resuspended at 40 U/ml in the Afinion™ CRP lysis buffer for various periods of time up to 18 hours at 22 degrees C. before analysing the blood sample containing elevated white blood cells.

| Time | 5 min | 60 min | 120 min | 18 hours |
|---|---|---|---|---|
| Relative Activity | 100% | 104% | 94% | 61% |

It is demonstrated that the Benzonase™ appears stable in an aqueous suspension for less than 1 day. A decrease in activity is noted after 120 min.

B—Frozen and freeze-dried Benzonase™ beads, prepared as in Example 7 and placed in the Afinion™ CRP cartridge as described above, were incubated for up to 2 months at 4, 22 or 37 degree C. for various time periods before analysing a blood sample containing elevated white blood cells.

| Temp | Day 0 | 1 month | 2 month |
|---|---|---|---|
| 4 C. | 100 | 99 | 96 |
| 22 C. | 100 | 100 | 105 |
| 37 C. | 102 | 98 | 99 |

Benzonase ™ appears stable as a frozen and freeze-dried bead for months.

The invention claimed is:

1. An automated membrane assay method for at least one non-nucleic acid component of a whole blood sample, said method comprising:
    treating said sample under conditions whereby to cause cell lysis thereby breaking up substantially all of the cellular membranes and nuclear membranes,
    subjecting the thus-generated lysed sample to conditions causing cleavage of nucleic acid molecules, and
    flowing the lysed sample through a membrane of a pore size no greater than 10 µm having immobilized thereon a specific binding ligand for the component of the sample and assaying that part of the sample retained on or by the membrane for the component of said sample, wherein said cleavage of nucleic acid molecules is provided by radiative conditions, chemical conditions and/or biological conditions.

2. The method as claimed in claim 1 wherein said biological conditions are provided by a biological reagent comprising a nuclease selected from micrococcal nuclease, S1 Nuclease, Mung Bean Nuclease, DNase I, Nuclease BAL 31 and Benzonase™.

3. The method as claimed in claim 2 wherein said nuclease is provided in dried form.

4. The method as claimed in claim 1 wherein cell lysis is detergent lysis, hypotonic lysis, hypertonic lysis or chaotropic lysis.

5. The method as claimed in claim 4 wherein said lysis is provided by a detergent selected from cationic surfactants, anionic surfactants, zwitterionic surfactants and non-ionic surfactants.

6. A method of claim 1, wherein said nucleic acid cleavage conditions comprise:
    (a) reduced membrane blockage;
    (b) reduced assay time; or
    (c) increased processible sample volume.

7. The method as claimed in claim 1, wherein said one non-nucleic acid component is selected from the group consisting of small molecules, amino acids, co-factors, vitamins, oligo-peptides, poly-peptides, antibodies, proteins, protein complexes, peptide hormones, non-peptide hormones and acute-phase markers.

8. The method as claimed in claim 1, wherein said non-nucleic acid component is selected from the group consisting of C-reactive protein (CRP), cobalamin, transcobalamin, homocysteine, folate, folate receptors and combinations thereof.

9. The method as claimed in claim 8, wherein said non-nucleic acid component is CRP.

10. A membrane assay method for a non-nucleic acid component of a whole blood sample, said method comprising:
    treating said sample under conditions whereby to cause cell lysis thereby breaking up substantially all of the cellular membranes and nuclear membranes,
    subjecting the thus-generated lysed sample to enzymatic conditions causing cleavage of nucleic acid molecules, and
    flowing the lysed sample through a membrane of a pore size no greater than 10 µm having immobilized thereon a specific binding ligand for the component of the sample and assaying that part of the sample retained on or by the membrane for the component of said sample.

11. The method as claimed in claim 10 wherein said enzymatic conditions are provided by a biological reagent comprising a nuclease selected from micrococcal nuclease, S1 Nuclease, Mung Bean Nuclease, DNase I, Nuclease BAL 31 and Benzonase™.

12. The method as claimed in claim 11 wherein said nuclease is provided in dried form.

13. The method as claimed in claim 10 wherein cell lysis is detergent lysis, hypotonic lysis, hypertonic lysis or chaotropic lysis.

14. The method as claimed in claim 10 wherein said lysis is provided by a detergent selected from cationic surfactants, anionic surfactants, zwitterionic surfactants and non-ionic surfactants.

15. The method as claimed in claim 10, wherein said non-nucleic acid component is selected from the group consisting of C-reactive protein (CRP), cobalamin, transcobalamin, homocysteine, folate, folate receptors and combinations thereof.

* * * * *